(12) United States Patent
Stern et al.

(10) Patent No.: US 7,233,312 B2
(45) Date of Patent: Jun. 19, 2007

(54) SYSTEM AND METHOD FOR OPTIMAL VIEWING OF COMPUTER MONITORS TO MINIMIZE EYESTRAIN

(75) Inventors: Roger A. Stern, Cupertino, CA (US); Jory E. Moon, Los Altos, CA (US); Sherwyne Bakar, Palo Alto, CA (US)

(73) Assignee: Panaseca, Inc., Mountain View, CA (US)

( * ) Notice: Subject to any disclaimer, the term of this patent is extended or adjusted under 35 U.S.C. 154(b) by 0 days.

(21) Appl. No.: 09/920,337

(22) Filed: Jul. 31, 2001

(65) Prior Publication Data

US 2002/0047828 A1    Apr. 25, 2002

Related U.S. Application Data

(63) Continuation of application No. 09/680,573, filed on Oct. 6, 2000, now Pat. No. 6,592,223.

(60) Provisional application No. 60/222,268, filed on Jul. 31, 2000.

(51) Int. Cl.
  *G09G 5/00* (2006.01)
  *A61B 3/00* (2006.01)
(52) U.S. Cl. ..................... 345/156; 351/200
(58) Field of Classification Search ........ 345/156–158; 351/200, 222, 237, 239, 243, 246; 748/602, 748/744
  See application file for complete search history.

(56) References Cited

U.S. PATENT DOCUMENTS

| | | | |
|---|---|---|---|
| 4,437,032 A | 3/1984 | Gelhard | |
| 4,832,419 A * | 5/1989 | Mitchell et al. | 361/681 |
| 5,078,486 A | 1/1992 | Evans | |
| 5,121,981 A | 6/1992 | Waltuck et al. | |
| 5,355,180 A | 10/1994 | Back | |
| 5,367,315 A * | 11/1994 | Pan | 345/156 |
| 5,367,614 A | 11/1994 | Bisey | |
| 5,483,689 A | 1/1996 | O'Donnell et al. | |
| 5,592,285 A | 1/1997 | Pund | |
| 5,596,379 A | 1/1997 | Kawesch | |
| 5,668,743 A * | 9/1997 | Kushelvesky | 702/158 |
| 5,686,940 A * | 11/1997 | Kuga | 345/156 |
| 5,777,720 A | 7/1998 | Shapiro et al. | |
| 5,838,424 A * | 11/1998 | Wawro et al. | 351/245 |
| 5,854,661 A * | 12/1998 | Kochanski | 348/602 |
| 5,877,841 A * | 3/1999 | Jeon | 351/237 |
| 6,007,038 A | 12/1999 | Han | |
| 6,076,928 A * | 6/2000 | Fateh et al. | 351/203 |

(Continued)

FOREIGN PATENT DOCUMENTS

JP        08-292752     * 11/1996

(Continued)

*Primary Examiner*—Alexander Eisen
(74) *Attorney, Agent, or Firm*—Robins & Pasternak LLP

(57) ABSTRACT

A system and method for helping ensure that a user of a computer is set up to optimally view the computer monitor under optimal conditions in order to minimize eyestrain. The system includes determining an optimal viewing distance and monitoring the distance of a user from the computer monitor during use of the computer. The system further includes notifying the user when they stray from the optimal viewing distance and further may include testing various aspects of the user's eyesight during use of the computer monitor.

31 Claims, 5 Drawing Sheets

View of system in place on a computer

U.S. PATENT DOCUMENTS

| | | |
|---|---|---|
| 6,134,335 A | 10/2000 | Yang |
| 6,148,331 A | 11/2000 | Parry |
| 6,244,711 B1 | 6/2001 | Fateh et al. |
| 6,350,032 B1 | 2/2002 | Menozzi et al. |
| 6,433,759 B1 * | 8/2002 | Richardson et al. ........... 345/7 |
| 6,592,223 B1 * | 7/2003 | Stern et al. ................. 351/239 |
| 6,606,130 B1 * | 8/2003 | George ....................... 348/744 |
| 6,690,351 B1 * | 2/2004 | Wong ......................... 345/156 |

FOREIGN PATENT DOCUMENTS

JP          2000-098991      *    4/2000

* cited by examiner

View of system in place on a computer

Side view, showing sensing distance to user's head

SYSTEM AND METHOD FOR OPTIMAL VIEWING OF COMPUTER MONITORS TO MINIMIZE EYESTRAIN

CROSS-REFERENCE TO RELATED APPLICATIONS

This application is a continuation of U.S. patent application Ser. No. 09/680,573, filed Oct. 6, 2000 (now U.S. Pat. No. 6,592,223, issued Jul. 15, 2003) and claims the benefit of provisional application 60/222,268, filed Jul. 31, 2000, which applications are hereby incorporated by reference in their entireties herein.

BACKGROUND OF THE INVENTION

1. Field of the Invention

The present invention relates to systems and methods for helping ensure that a user of a computer is properly positioned to view a monitor, and more particularly, to systems and methods for helping ensure that a user of a computer is set up to optimally view the computer monitor under optimal conditions.

2. Description of the Prior Art

A common problem of many computer users is that they often sit too close to the computer monitor. This is especially true of young children. It is well known that if one sits too close to the computer monitor, the eye will intently focus on what is many times a stationary image. This can lead to eyestrain.

Additionally, many users sit too long in front of a computer without taking a break. This is true for many workers who must operate a computer for almost the entire work day. It is often difficult to ascertain when one has spent too much time in front of a computer without taking a break. Additionally, many times the lighting in the room where the computer is located may not be optimal. This may lead to glare and other problems that also result in eyestrain.

Recent medical literature clearly shows an increase in eyestrain-related problems, especially in children. Use of computers is rapidly growing among children and improper use of computers is thought to be a contributing factor to the increase in eyestrain related problems in children.

SUMMARY OF THE INVENTION

In accordance with one embodiment of the present invention, a user of a computer monitor determines a proper viewing distance. This may be accomplished by an installation program that will ask the user to select a viewing distance by displaying any one of a number of standard test patterns and asking the user to identify them. The optimal viewing distance would then be selected based upon the identification of the test patterns and would preferably be slightly close than the farthest distance at which the user can correctly identify the test pattern.

In accordance with another embodiment of the present invention, the user will be notified when he is not at the proper viewing distance. This may be accomplished by switching the computer monitor's display to a "screensaver"-type program, sounding an alarm, or even turning off the computer monitor. A sensor may be provided for monitoring the actual distance of the user. Preferably, the sensor would be "piggybacked" onto an existing device, such as, for example, a keyboard or mouse, thus not requiring any additional computer resources or requiring any other source of electrical power.

In accordance with another embodiment of the present invention, statistics about a user's viewing distance are recorded. This may be especially useful in work situations where almost continuous use of the computer is anticipated. For example, there might be trend toward closer viewing as the length of time the computer is being used increases. In such a situation, this may indicate that a break is in order, and in a preferred embodiment of the present invention, the system would so notify the user.

In accordance with another embodiment of the present invention, the measured viewing distance may be used for a periodic test of the user's eyesight. For example, test patterns may be displayed and the user may be "scored" at some predetermined fixed distance. If the user scores too low on the tests, use of the computer may be inhibited.

In accordance with another embodiment of the present invention, the level of ambient light in the user's environment may be measured and suggestions may be provided by the system to either increase or decrease the amount of ambient light. In such an embodiment, a light level sensor may be incorporated into the system that would feed information regarding the ambient light into the computer through the shared interface as previously discussed.

In accordance with yet another embodiment of the present invention, the system may determine "amplitude of accommodation," which is the minimum distance between the eye and a viewing surface below which the surface is blurry.

In accordance with yet another embodiment of the present invention, a user may be presented with color tests and asked to respond to them. This may be done over a period of time to determine the user's interpretation of colors as use of the computer over the period of time progresses.

In yet another embodiment of the present invention, the system monitors the number of times or rate at which an individual blinks their eyes. The individual may be viewing a monitor and with a sensor, the rate of blinking of the eyes is monitored. By monitoring the rate at which the individual blinks their eyes, or by monitoring the rate of changes in a baseline eye blink rate, early detection of visual fatigue is possible.

DETAILED DESCRIPTION OF THE PREFERRED EXEMPLARY EMBODIMENTS

Figure 1:
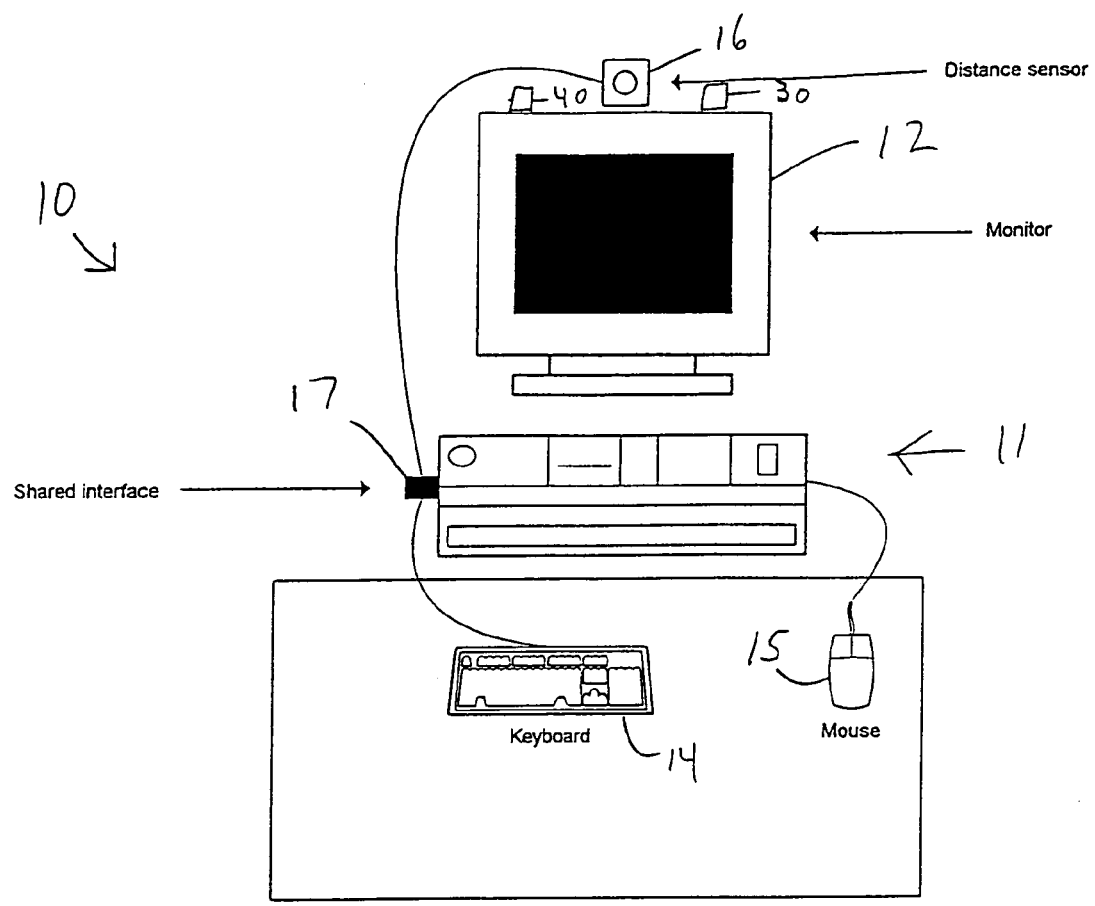
FIG. 1 is a schematic illustration of a system in accordance with the present invention with a computer system.
Figure 2:
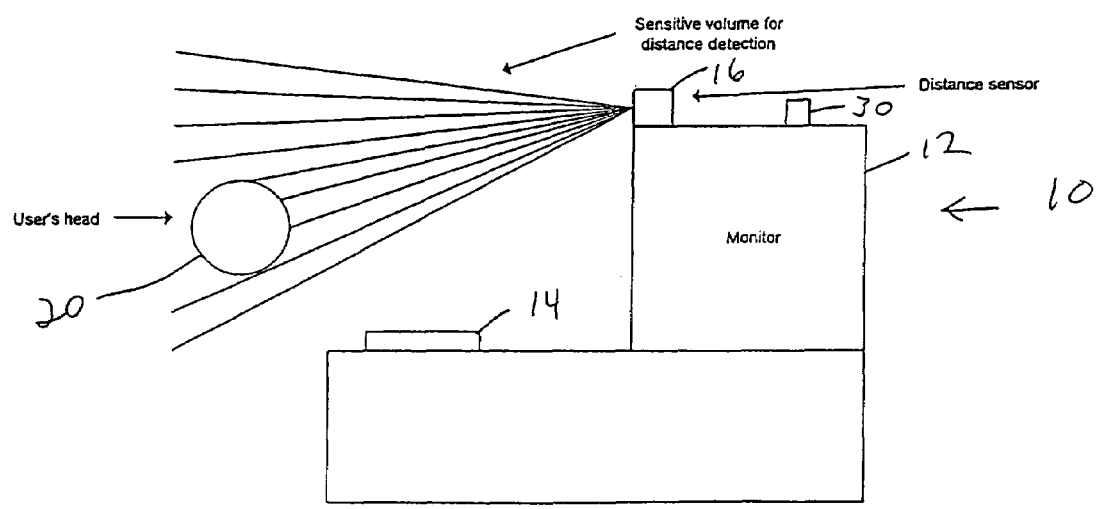
FIG. 2 is a side view of the system illustrated in FIG. 1.

FIGS. 1 and 2 schematically illustrate a possible arrangement of a system 10 in accordance with the present invention. System 10 is depicted as a computer system 11 including a computer monitor 12. Those skilled in the art will understand that other monitors will also benefit from the methods and system of the present invention. However, for simplicity and clarity, a computer system will be used to describe the present invention.

System 10 further includes computer inputs, such as, for example keyboard 14 and mouse 15. System 10 further includes at least one distance sensor 16. Preferably, distance sensor 16 is piggybacked with, for example, the keyboard or the mouse via a shared interface 17. Thus, the distance sensor does not take up additional computer resources or require any additional source of electrical power. More distance sensors may be used and may be arranged in various configurations as needed.

Distance sensor 16 may be one of any of well-known distance sensors in the art. In a preferred embodiment, the use of echolocation with high frequency sound waves is used. As stated previously, preferably, distance sensor 16 is piggybacked with an existing computer peripheral with a shared interface. However, distance sensor 16 may be interfaced to the computer through its own interface port, such as, for example, an RS 232 serial port. Distance sensor 16 may be mounted on the monitor using an adhesive tape attachment and aimed such that the spatial volume where the distance measurements are made extend from a point very close to the monitor, for example, within 6 inches and extend out to what may be considered the farthest practical viewing distance, for example, 36 inches. Generally, optimal viewing distance is believed to be approximately 18 to 21 inches from computer monitor 12. The distance information from the sensor may be sampled, for example, once per second, and such real-time distance data is then fed directly into the computer through the interface.

In an initial step, a user 20 determines their proper viewing distance. This may be accomplished with an installation program that will ask the user to select a viewing distance. In a preferred embodiment, the optimal viewing distance would be user specific for computers used by more than one person. Preferably, the method includes displaying any one of a number of standard test patterns that are known in the art and asking the user to identify them. Preferably the optimal viewing distance is then set slightly closer then the farthest distance at which the user is able to correctly identify the test pattern.

System 10 will preferably then notify user 20 when they are not at the proper viewing distance as measured by distance sensor 16. One way in which user 20 may be notified is by switching the display to a "screensaver" type of program when the user gets too close to the screen. Preferably, the switching algorithm used to switch to the screensaver would be intelligent and, for example, ignore momentary infrequent violations of distance limits. The type of screensaver may be selected by the user and, for example, may consist of a message indicating that the user is too close or the image may consist of a relaxing image that is pleasant to view. In any event, normal use of the computer is suspended until the user returns to the proper viewing distance or until sometime when it expires. If user 20 is a child, the screensaver may be some type of gentle reminder to move back from the computer, either visual or auditory, or it may be done with animated characters, or by motivation such as a game where the child receives points or a "gold star" if the proper viewing distance is maintained.

In accordance with another embodiment of the present invention, statistics are recorded about user 20's viewing distance, as measured by distance sensor 16. The statistics may then be monitored or analyzed in order to determine if there is a trend toward closer viewing and the length of time that the computer monitor is being viewed. This information may be used to indicate that a break is in order and, preferably, the system would notify user 20, for example, either visually or audibly.

Furthermore, the measured viewing distance may be used for a periodic test of the user's eyesight. This may be used by displaying test patterns already known in the art similar to those used above for determining optimal viewing, and "scoring" the user at some predetermined fixed distance. If user 20 scores too low on such a test, use of the computer may be inhibited. Additionally, in a preferred embodiment of the present invention, a light sensor 30 is provided that measures the level of ambient light in the user's environment and provides suggestions as to either increasing or decreasing the amount of ambient light. Light level sensor 30 may be incorporated into distance sensor 16 or may be a separate sensor all together. If it were a separate sensor, light level sensor 30 once again would preferably be piggybacked with another device in the system or may have a dedicated interface, such as, for example, an RS 232 serial port.

Additionally, system 10 preferably measures a user's "amplitude of accommodation," which is generally defined as the minimum distance between the eye and a viewing surface below which the surface is blurry. Such a test for amplitude of accommodation preferably is performed by having the user lean forward until the screen becomes fuzzy. While the user is at this distance where the screen has become fuzzy, the user clicks the mouse and the software measures the distance to the user via the distance sensor 16. Such a test may be performed over a period of time in order to determine the variance of the amplitude of accommodation over a period of time of use of the computer monitor.

In another embodiment of the present invention, system 10 performs color testing of the user. User 20 is preferably presented with color tests, which are known in the art, and is asked to respond to them. As with the amplitude of accommodation test, this may be performed over a period of time in order to determine the variance of the user's "interpretation" of colors over a period of time of use of the computer monitor.

System 10 also preferably monitors a user's number of times of blinking, or rate at which the user blinks their eyes. In such an embodiment, system 10 includes a small imaging sensor or camera 40 pointed at the user's face. An image analysis and pattern recognition algorithm is used to identify the user's face from other objects in a room, identify the eyes on the face and make a decision as to whether the eyes are open or not. Small digital image sensors and powerful digital signal processing circuitry is available to perform these functions and is well known in the art. Performance of the system may be improved or made user specific, for example, by having the computer user let the system take reference images of the face with their eyes both open and closed. These reference images then serve as templates in a pattern matching algorithm.

In a further embodiment of the present invention, system 10 includes testing or determining a user's visual acuity. Such testing, which may commonly be referred to as rapid visual acuity testing (RVAT) would be useful for determining the visual acuity of a user at the user's working distance from the computer monitor. The visual acuity may be monitored periodically in order to determine changes over a period of time. In a preferred embodiment, user 20 would sit at their normal working distance at the computer and the screen would be blank except for arrows on an outer portion of the screen that act as indicators for a band or ring or "C." The "C" appears on the screen as a 20/10 letter (i.e., a size of a letter that at 20 feet would appear to a user as being at 10 feet) and would slowly increase in size, for example, 20/11, 20/12. 20/13, etc., until first discernable by the user. At the point the user detects the "C," the user clicks the mouse or the enter key. The progression of the C pauses and a message appear instructing the user to identify the position of the C. If the answer is correct, the "C" is rotated randomly in two more positions. If the individual again correctly identifies the orientation of the "C," then the test is ended. Preferably, a predetermined amount of time, for example, up to five seconds for each decision, is provided.

By accurately knowing the distance of the eye from the computer, size of the "C" angular subtends, and the correct response, a software program within the computer will be able to calculate an individual's visual acuity. If improper responses are made, then the progression of size of the "C" slowly increases until the right answers are given.

By calculating the level of illumination, the testing of visual acuity may be performed at the same level of light.

Figure 3:
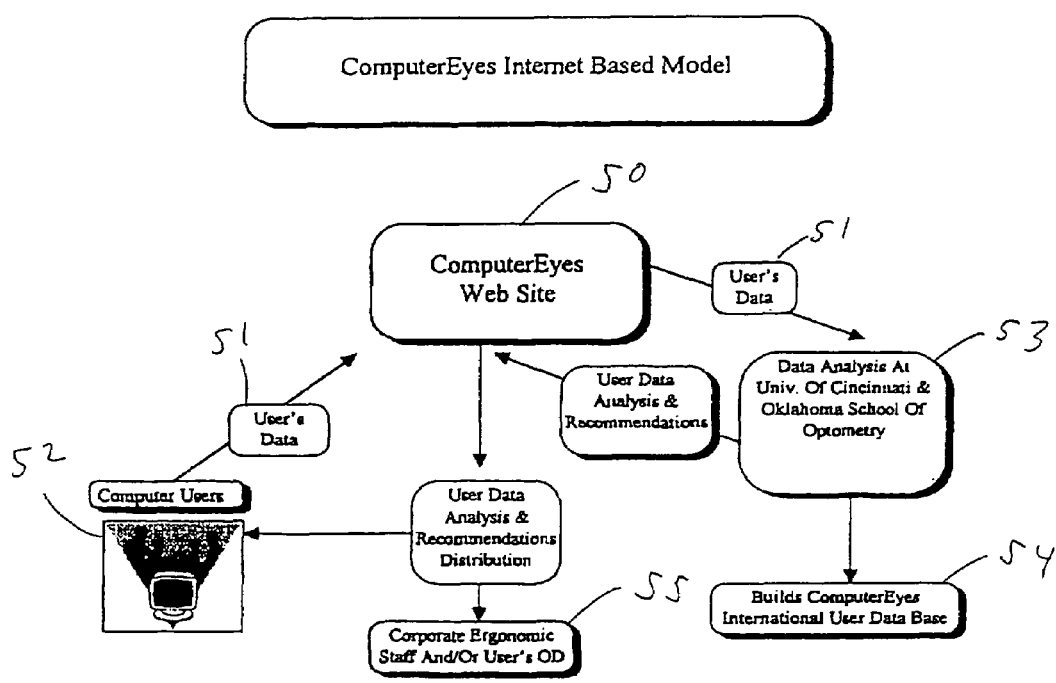
FIG. 3 is a schematic illustration of an internet-based model of a system in accordance with the present invention.

FIG. 3 illustrates a schematic illustration of an Internet based model of the system in accordance with the present invention. A central web site 50 is provided for receiving data 51 from a user at a local site 52 that includes computer users. The computer user's data is sent to the central web site over the Internet and then forwarded to an analysis location 53 that analyzes the user's data. The data analysis site also provides a central web site international users' database 54 and sends back analyses and recommendations regarding the user data to the central web site. The central web site then distributes the data analysis and recommendations to a corporate ergonomic staff and/or users' OD 55 and, if desired, to the actual user itself.

Figure 4:
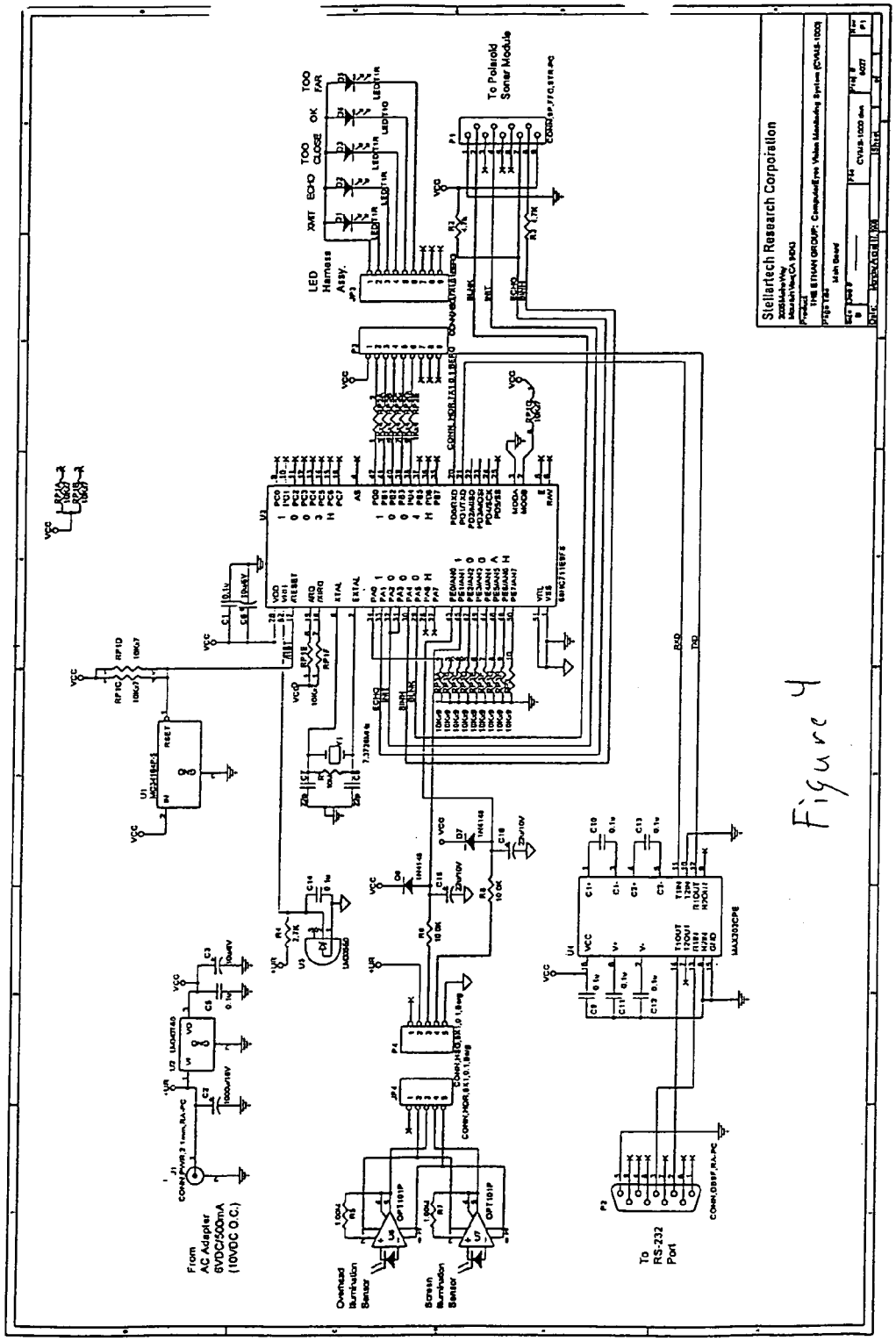
FIG. 4 is a schematic illustration of a circuit for a motherboard in accordance with the present invention.
Figure 5:
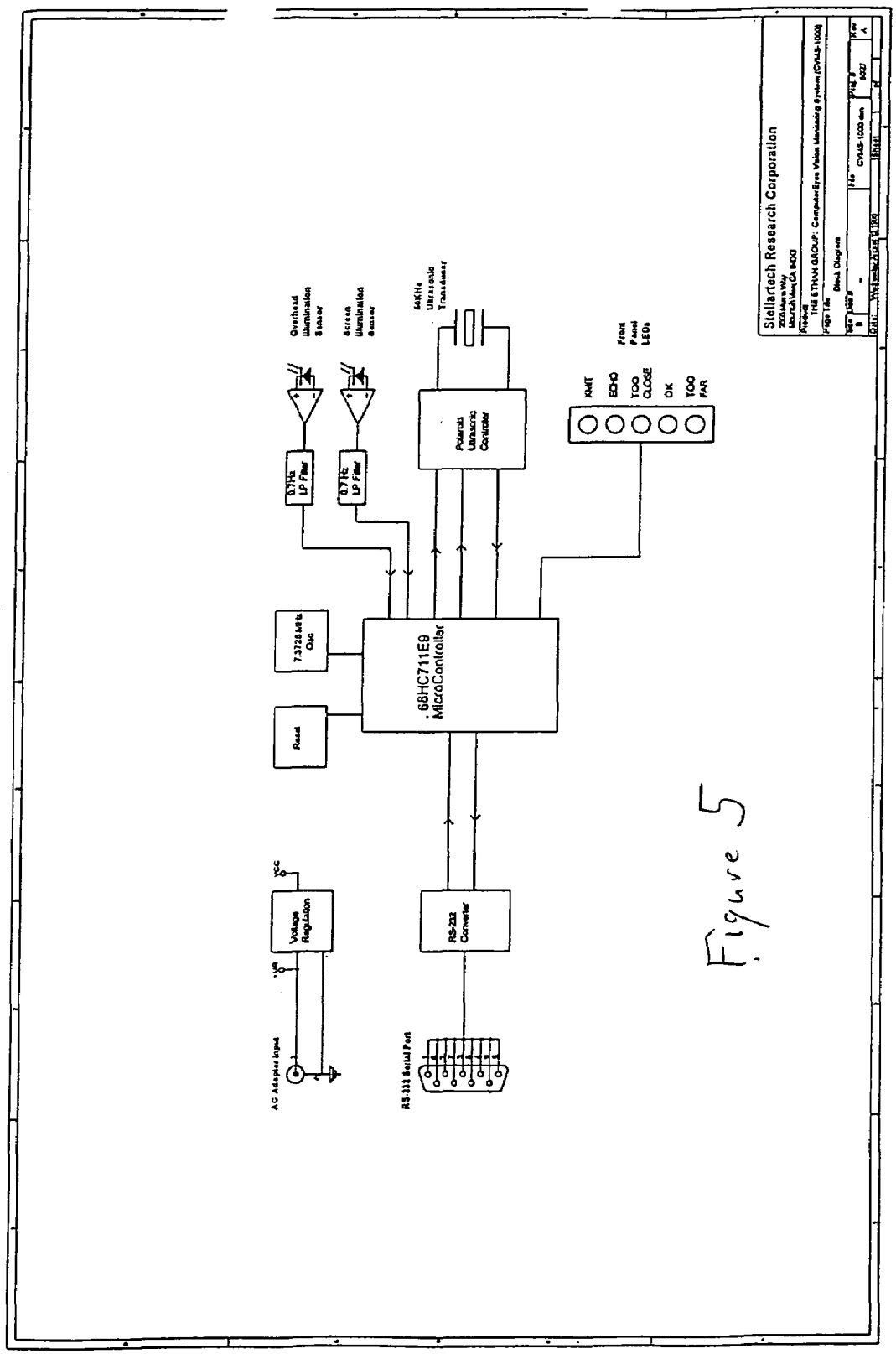
FIG. 5 is a schematic block diagram of a possible arrangement of a control system for a system in accordance with the present invention.

FIG. 4 schematically illustrates a possible circuit for a motherboard that would be included in a computer system that utilizes the present invention. FIG. 5 is an electronic block diagram of a possible control system for a system in accordance with the present invention.

The present invention may also be used for vision testing in the home for those patients who have recently undergone ocular surgery, require monitoring before surgery, are taking pharmaceuticals that may affect their vision, or have an ongoing medical problem that is vision related.

Preferably, the system resembles a laptop computer incorporating the appropriate hardware features plus a keyboard for user input and a remote input device for distance vision testing. The system also preferably includes a built-in modem configured to automatically access a web site on the click of the mouse.

Software features preferably include user medical history, medications, and vision profiling, real time measurement of viewing distance while vision testing, adjusting test pattern size relative to viewing distance, recommendations for optimizing environmental lighting prior to vision testing, recording and tracking real time user vision performance over time, and transmitting patient information and analysis to eyecare and/or medical doctor.

In the software, preferably an icon in the utility tray will be incorporated to activate onscreen directions, comments and recommendations based upon the system's data analysis. Furthermore, the software will preferably make productivity measurements by evaluating typing speed, mouse clicks, engagement time and errors. Additionally, the view size will preferably increase automatically, over time, based upon collected parameters and analyzed data provided by the software.

The system preferably allows a patient's professional caregiver to prescribe the type and frequency of vision testing. Upon test completion, the patient plugs the device into a standard phone outlet to transmit the data to the web site where it is stored in the patient's file and transmitted either by e-mail or fax to their doctor(s).

Preferably, the system includes three or more light meters in order to determine the source of multi-directional light relative to the user. This allows for the analysis of glare. Preferably, one separate attachable sensor is used to measure various parameters of the monitor screen. One or more of these may be attached to a retractable cable that allows it to be moved and possibly positioned facing the user's monitor to measure the brightness of the screen.

Preferably, the system includes sensors to measure ambient noise, temperature and humidity. Such information allows for proper operation of the equipment and also allows for the analysis to take into account the effects of these conditions.

While the system has been described throughout with the use of software, in an alternative embodiment, the system will be in communication with a central website. Such communication may be provided, for example, via the Internet. The website would thus control the system and various parameters may be automatically changed within the system as directed from the website, such as, for example, the viewer distance from the monitor.

The system also preferably includes a leveling device for proper positioning of the individual in front of the computer. LEDs may be incorporated into the system in order to determine the correct viewing angle for the individual.

Additionally, the system preferably includes a mechanical apparatus situated under a user's monitor or incorporated into a user's desk. The apparatus automatically moves the computer monitor (including flat panel displays) in a forward or backward direction to adjust for accommodative and visual changes of the user throughout the day. The image size or view size on the user's screen will also adjust automatically in accordance with the direction of monitor display movement. The mechanical apparatus also preferably will control the height of the monitor and the viewing angle of the monitor.

In some embodiments, the position of the monitor in one, two or three dimensions is controlled to reduce eyestrain, improve viewing, relax or exercise head, neck or other muscles or relieve or ameliorate strain on muscles. The position might be changed to an identified optimal position or might change among several positions to provide variability or exercise of selected muscles or reduction of strain on body parts.

What is claimed is:

1. A system for monitoring the use of a display by a user using the display for performance of a task, the system comprising: a display; a first sensor positioned close to the display and selected from the group consisting of a distance sensor and a light sensor; and a software program for processing inputs from the first sensor and for displaying a test pattern on the display, wherein the distance sensor measures viewing distance, the light sensor measures ambient light, and wherein the test pattern is a test pattern usable for at least one test selected from the group consisting of a visual acuity test, a visual field test, an amplitude of accommodation test, and a color sensitivity test.

2. The system of claim 1, further comprising a communication link between the system and a computer system accessible using a hypertext protocol.

3. The system of claim 1, wherein the display is selected from the group consisting of a CRT monitor, an LCD monitor and a flat panel.

4. The system of claim 1, wherein the first sensor is incorporated into a bezel of the display or structure supporting the display.

5. The system of claim 1, further comprising at least three light sensors positioned to determine a source of multidirectional light relative to the user.

6. The system of claim 1, further comprising a computer for processing inputs from the first sensor.

7. The system of claim 1, further comprising a cable coupling the first sensor to the system.

8. The system of claim 1, wherein the first sensor is positioned to monitor the display.

9. The system of claim 1, wherein the first sensor is positioned on top of the display.

10. The system of claim 1, further comprising a remote input device.

11. The system of claim 1, wherein the first sensor is a distance sensor.

12. The system of claim 1, wherein the first sensor is a light sensor.

13. A system for monitoring the use of a display by a user, the system comprising a display used by the user for performance of a task; a first sensor positioned relative to the display and selected from the group consisting of a distance sensor and a light sensor; and a means for automatically notifying user when user is not at a proper viewing distance; wherein the means for notifying user comprises switching the display to a screensaver type, wherein the first sensor includes an incorporated camera or incorporated imaging sensor, and wherein the incorporated camera or incorporated imaging sensor is capable of monitoring blink rate.

14. A system for monitoring the use of a display by a user, the system comprising a display used by the user for performance of a task; first sensor positioned relative to the display and selected from the group consisting of a distance sensor and a light sensor; and a means for automatically notifying user when user is not at a proper viewing distance wherein the means for notifying user comprises switching the display to a screensaver type, wherein the switching comprises use of a switching algorithm, and wherein the switching algorithm ignores momentary infrequent violations of distance limits.

15. The system of claim 14, further comprising a communication link between the system and a computer system accessible using a hypertext protocol.

16. The system of claim 14, wherein the display is selected from the group consisting of a CRT monitor, an LCD monitor and a flat panel.

17. The system of claim 14, wherein the first sensor is incorporated into a bezel of the display or structure supporting the display.

18. The system of claim 14, wherein the first sensor is a distance sensor.

19. The system of claim 14, wherein the first sensor is a light sensor.

20. A system for monitoring the use of a display by a user, the system comprising a display used by the user for performance of a task; first sensor positioned relative to the display and selected from the group consisting of a distance sensor and a light sensor; and a means for automatically notifying user when user is not at a proper viewing distance; wherein the means for notifying user comprises switching the display to a screensaver type, and wherein normal use of the system is suspended until user returns to a proper viewing distance or until a lapse of time.

21. The system of claim 20, further comprising a communication link between the system and a computer system accessible using a hypertext protocol.

22. The system of claim 20, wherein the display is selected from the group consisting of a CRT monitor, an LCD monitor and a flat panel.

23. The system of claim 20, wherein the first sensor is incorporated into a bezel of the display or structure supporting the display.

24. The system of claim 20, wherein the first sensor is a distance sensor.

25. The system of claim 20, wherein the first sensor is a light sensor.

26. A system for monitoring the use of a display by a user, the system comprising: display used by the user for performance of a task; a first sensor positioned relative to the display and selected from the group consisting of a distance sensor and a light sensor; and a means for automatically notifying user when user is not at a proper viewing distance, wherein the first sensor includes an incorporated camera or an incorporated imaging sensor which is capable of monitoring blink rate.

27. The system of claim 26, further comprising a communication link between the system and a computer system accessible using a hypertext protocol.

28. The system of claim 26, wherein the display is selected from the group consisting of a CRT monitor, an LCD monitor and a flat panel.

29. The system of claim 26, wherein the first sensor is incorporated into a bezel of the display or structure supporting the display.

30. The system of claim 26, wherein the first sensor is a distance sensor.

31. The system of claim 26, wherein the first sensor is a light sensor.

* * * * *